United States Patent [19]
Vanderlaan et al.

[11] Patent Number: 5,053,336
[45] Date of Patent: Oct. 1, 1991

[54] MONOCLONAL ANTIBODIES FOR THE SEPARATE DETECTION OF HALODEOXYURIDINES AND METHOD FOR THEIR USE

[75] Inventors: Martin Vanderlaan, Danville; Bruce E. Watkins; Larry H. Stanker, both of Livermore, all of Calif.

[73] Assignee: Regents of the University of California, Oakland, Calif.

[21] Appl. No.: 380,638

[22] Filed: Jul. 17, 1989

[51] Int. Cl.$^5$ .................. C12N 5/00; C12N 15/00; C07K 15/14
[52] U.S. Cl. ................. 435/240.27; 435/172.2; 530/387; 530/809; 935/95; 935/103
[58] Field of Search .............. 435/240.26, 240.27, 435/172.2, 6, 7; 436/548; 530/387, 808, 809; 935/103, 107, 110, 95, 106

[56] References Cited

U.S. PATENT DOCUMENTS 4,529,700 7/1985 Gratzner ................. 435/240.27
4,812,394 3/1989 Dolbeare et al. ................. 435/7

OTHER PUBLICATIONS

Halloran et al., "The Preparation of Nucleotide-Protein Conjugater: Carbodiimides as Coupling Agents", J. Immunology; vol. 99, pp. 373-377.
Vanderlann et al., "Improved High-Affinity Monoclonal Antibody to Iododeoxyuridine"; Cytometry, vol. 7; pp. 499-507 (1986).
Golumbeski, Jr. et al., Analytical Biochemistry, vol. 154, 1986, pp. 373-381.
Edward S. Golieb, "The Cellular Basis of the Imune Response: An Approach to Immunology", 1977, Sinauer Associates, Inc., Sunderland, Mass., pp. 248-252.
Campana, D., E. Coustan-Smith and G. Janossy, "Double and Triple Staining Methods for Studying the Proliferative Activity of Human B and T Lymphoid Cells", J. Immunological Methods 107: 79-88 (1988).
Kuo, W.-L., F. Dolbeare, M. Pallavicini and J. W. Gray "Cell Kinetic Studies of the BN Myelocytic Leukemia Labeled with Bromo- and Iodo-deoxyuridine Before and After Multiple Treatment of 1-B-D-Arabinofuranosycytosine", Lawrence Livermore National Laboratory Report No. UCRL-101039, Abstract.
Dolbeare, F., W.-L. Kuo, W. Beisker, M. Vanderlaan and J. W. Gray, "Current Methods in Using Monoclonal Antibodies to do Halopyrimidine/DNA Analysis by Flow Cytometry", Lawrence Livermore National Laboratory Report No. UCRL-100510, Abstract.

Primary Examiner—Esther L. Kepplinger
Assistant Examiner—Florina B. Hoffer
Attorney, Agent, or Firm—Henry P. Sartorio; Leona L. Lauder; Nora A. Hackett

[57] ABSTRACT

Monoclonal antibodies are described which have specific affinities for halogenated nucleoside analogs and are preferentially selective for one particular halogen. Such antibodies, when incorporated into immunochemical reagents, may be used to identify and independently quantify the cell division character of more than one population or subpopulation in flow cytometric measurements. Independent assessment of division activity in cell sub-populations facilitates selection of appropriate time and dose for administration of anti-proliferative agents. The hybridomas which secrete halogen selective antibodies and the method of making them are described.

2 Claims, 7 Drawing Sheets

MONOCLONAL ANTIBODIES FOR THE SEPARATE DETECTION OF HALODEOXYURIDINES AND METHOD FOR THEIR USE

The United States Government has rights in this invention pursuant to Contract No. W-7405-ENG-48 between The Regents of the University of California and the United States Department of Energy.

The subject invention is related generally to monoclonal antibodies and method for their use to measure DNA precursor incorporation activity and more particularly to monoclonal antibodies which are specifically reactive with nucleoside analogs containing different halogens and to a method for their use in measurement of DNA precursor incorporation.

IDENTIFICATION OF TERMS

Abbreviations or definitions used in the disclosure herein are as follows:
- BrdU, bromodeoxyuridine; IdU, iododeoxyuridine;
- BrdUMP, 5-bromo-2'-deoxyuridine-5-monophosphate;
- IdUMP, 5-iodo-2'-deoxyuridine-5-monophosphate;
- FldUMP, 5-fluoro-2'-deoxyuridine-5-monophosphate;
- CldUMP, 5-chloro-2'-deoxyuridine-5-monophosphate;
- dUMP, deoxyuridine-5-monophosphate;
- dTMP, deoxythymidine-5-monophosphate
- ELISA, competition enzyme-linked immunosorbent assay;
- KLH, keyhole limpet hemocyanin;

BACKGROUND OF THE INVENTION

This invention relates to suitable reagents and methods by which cell kinetics analysis may be performed on more than one population at the same time. Cell cycle kinetics analysis techniques may be used for identification of the cell proliferative status of normal and tumor tissue. The characterization of labeled precursor incorporation into DNA of growing cells provides a means to determine the portion of the tissue population which comprises the "growth fraction" of cells. DNA synthesis in a cell population can be estimated by measurement of the incorporation of labeled DNA precursor, nucleoside analogs. The nucleoside analogs comprise a nucleoside base, which may be pyrimidines and purines, which include, but are not limited to uracil, thymidine, cytosine, adenine and guanine or derivatives of these, that is bound to a pentose sugar, which may be deoxyribose or ribose. One or more substituents on these compounds may be a labeling atom. The labeled nucleoside analog may contain a radioactive atom or other detectable molecules. The size and the activity of a proliferative cell fraction may be estimated by measurement of labeled compound incorporation when cell DNA is sampled at one or more later times following the administration of a labeled nucleoside analog pulse.

This invention provides materials which enable rapid and specific measurement of cell division activity in more than one cell population. Measurements of the proportion of cells which are synthesizing DNA and the time of incorporation can be used to determine cell cycle traverse times for normal and malignant cells. Classical techniques for determination of the cell cycle include assessment of incorporated radiolabel into cell nuclei with detection by tedious autoradiographic techniques or by liquid scintillation spectrometry. The duration of the cell cycle and the fraction of cells undergoing replication in normal and malignant cells can be determined flow cytometrically by analysis of the distribution of the radiolabeled DNA which is undergoing DNA synthesis (S-phase DNA). (Latt, et al J. Histochem. Cytochem 25: 927–934 (1977)). Labor-intensive and time-consuming cytometric techniques have limited usefulness because they discriminate poorly between unlabeled or weakly labeled cells. Liquid scintillation DNA measurement techniques provide no information about the proliferative activity among individual cells or subpopulations of cells. Interpretation of DNA distribution provides no information about the absolute role of DNA synthesis.

The immunochemical reagents of this invention may be used for rapid detection of cell proliferation activity without the use of radiolabeled materials. DNA synthesis may be monitored by measurement of radiolabeled precursor incorporation in vivo or in vitro following injection of small pulses of radioactively labeled precursors, or several pulses of sequentially added radiolabeled precursors, used in combination. (Schultze, B. et al. (1976) Cell Tissue Kinetics 9: 245–255) Such a sampling procedure which uses incorporated radioactive label requires many hours, when measured with liquid scintillation counting, or many weeks when assayed in particular cell types on microscope slides by autoradiography. Analysis of DNA precursor incorporation with $^3$H-thymidine or $^{14}$C-thymidine provide sensitive in vitro indicators of DNA synthesis, but pose safety limitations when such precursors are used for in vivo sampling. Use of multiple radiolabeled precursors for in vivo sampling in the clinical setting has limited practicality, as multiple sampling is expensive and causes additional patient discomfort, as well as increases the patient's risk of excess radiation exposure.

The present invention relates to recent developments in fluorometric and flow cytometric procedures which overcome some of the limitations on the use of radiolabeled precursors for the detection and measurement of DNA synthesis. In the flow cytometric measurement technique of Dolbeare, et al. (U.S. Pat. No. 4,812,394), halogenated nucleotide DNA precursors are monitored as they are incorporated into DNA, by their binding to a halogen specific monoclonal antibody. Cells are grown in the presence of a halogenated DNA precursor and the DNA strands are partially denatured to allow access for the halogen-specific monoclonal antibody to bind to the incorporated DNA precursor. The presence of the halogen-specific monoclonal antibody is detected by complexing a fluorescent label to the antibody which is subsequently detected by flow cytometry. A separate fluorescent dye, for the total cellular DNA, is used as a reference standard so that cells with active DNA proliferation may be correlated with those of the rest of the cell population.

Because the currently available monoclonal antibodies do not descriminate between halogenated analogs incorporated into DNA, it has not heretofore been possible to identify more than one subpopulation of cells by monoclonal antibody binding to specific halogenated nucleic acid analogs. This invention overcomes the limitations of current immunochemical reagents to halogenated deoxyuridines which do not discriminate between analogs which contain different halogen moieties. Polyclonal antibodies to brominated nucleoside analogs, which were first available in the mid 1970's (Gratzner, et al 1975, 1976, 1978) did not have antigen specificity of monoclonal antibodies. Monoclonal antibodies to brominated nucleoside analogs were disclosed in the 1980's (Gratzner U.S. Pat. No. 4,529,700; Gratzner 1982; Vanderlaan 1985; Traincard, et al 1983; Gonchoroff 1985; Raza 1984) but these did not have the specificity necessary to discriminate sufficiently between nucleoside analogs which carried different halogen atoms, such as bromine, iodine, chlorine or fluorine. The antibodies to halogenated nucleoside analogs of previous studies did not discriminate between different halogen moieties on the nucleic acid precursor. Immunochemical reagents which bind to some degree to halogenated nucleoside analogs were developed by Gratzner, et al.(1985) (B-44) and Vanderlaan, et al. (1986) (IU-4). These monoclonal antibodies are commonly used in the flow cytometric measuring technique of Dolbeare et al, U.S. Pat. No. 4,812,394, for the measurement of incorporated DNA analog precursors and total cellular DNA, but are not sufficient to be used to distinguish between separate halogenated precursors which would indicate proliferative activity of separate subpopulations.

This invention provides a method to obtain information concerning the actively dividing cell populations in a malignant tissue. Such information is useful for the establishment of appropriate time and dose for administration of anti-cancer agents. Knowledge of the state of DNA replication in the cell populations enables a clinician to correlate the progress of the chemotheraputic treatment with the fraction of tumor cells synthesizing DNA, and the time of the DNA synthesis (S-phase) of the cell cycle. Effectiveness of cancer chemotherapy is improved by more precis establishment of the appropriate dose and time for administration of anti-proliferative agents. Analysis of the rate of precursor uptake permits estimation of the "growth fraction" and the duration of the resting or pre-synthesis phase, $G_1$; the DNA synthesis phase, S; and the division and reassembly phase, $G_2M$. These analyses may be done in vivo or in vitro, with cells isolated from the patient. Improvements in the assessment of the activity of dividing cell populations as enabled by this invention will increase the effectiveness of an appropriate cancer treatment program.

SUMMARY OF THE INVENTION

Accordingly, it is an object of the present invention to provide monoclonal antibodies, which are specific and sensitive for the detection of halogenated nucleoside analogs bearing different halogens. These antibodies can bind preferentially to designated halogenated nucleoside analogs even after they are incorporated into the DNA of different cell sub-populations. Incorporated nucleoside analogs bearing each different halogen can be detected during cytometric or flow cytometric analysis of cells by the halogen-specific immunochemical stains which comprise these monoclonal antibodies and an indicator molecule.

Another object is to provide hybridomas that produce monoclonal antibodies which will react specifically and sensitively with halogenated nucleoside analogs which have different halogen species.

Another object of the present invention is to provide a method of making monoclonal antibodies which will react specifically and sensitively with, and discriminate between halogenated nucleoside analogs which contain various halogens.

A further object is to provide a method for measurement of specific halogenated nucleoside analog incorporation by use of monoclonal antibodies which have preferred binding for a halogenated nucleoside analog, bearing a specific halogen. Use of immunochemical reagents for one or more specific halogens permits measurement of precursor incorporation into each of multiple cell subpopulations as a calibration of cell growth or cell growth inhibition.

Additional objects, advantages and novel features of the invention will be set forth in part in the description which follows, and in part will become apparent to those skilled in the art upon examination of the following and the accompanying drawings and their descriptions which form part of the disclosure herein and are incorporated herein by reference, or may be learned by practice of the invention. The objects and advantages of the invention may be realized by means of the methods and combinations particularly pointed out in the appended claims.

To achieve the foregoing and other objects and in accordance with the purpose of the present invention as embodied and broadly described herein, the subject invention is directed to monoclonal antibodies, and the hybridomas which produce them, which will differentially distinguish between various halogenated nucleoside analogs, specifically to brominated or iodinated compounds, more specifically to monoclonal antibodies which will distinguish between the halogenated deoxyuridines, bromodeoxyuridine and iododeoxyuridine and to the hybrid cell lines which are capable of continuously producing these antibodies. The invention is directed to the method for production of hybridomas which secrete monoclonal antibodies to halogenated nucleoside analogs and methods for identifying precursor incorporation into cell sub-populations by cytological or flow cytometry methods.

The method for the production of monoclonal antibodies which will distinguish between halodeoxyuridines, in accordance with the subject invention, comprises immunizing an animal that has been tolerized to a particular halogenated nucleoside analog, with a hapten which is a nucleoside analog that is halogenated with a different halogen than that used in the tolerization agent. In the stepwise procedure, an animal which has received tolerization agent is immunized by injection with a hapten that has been conjugated to a carrier protein. Sensitized immunoreactive cells, capable of producing antibodies responsive to the selected halogen of the immunizing antigen, are obtained from the animal, fused with immortally reproducing cells of the same species or of another animal species, and cultured in a suitable host or in a culture medium. The isolated clones of hybrid cells, refered to as hybridomas, continuously produce specific antibodies which react with the particular halogen of the immunizing antigen. Clones are screened and selected for those hybridomas which produce particular halogen-specific monoclonal antibodies These antibodies are harvested from the culture medium or from the host used for growing the cells, and purified, if desired.

According to a further aspect of the present invention, in accordance with its objects and purposes, the cell lines developed in accordance with the instant invention are capable of producing highly specific monoclonal antibodies which preferentially distinguish compounds containing different halogens on the nucleoside analogs even when the analogs are incorporated into DNA. A method using these halogen-specific antibodies is contemplated to be useful for the sensitive detection and characterization of multiple proliferating cell populations in a sample. More specifically, the subject method provides for a rapid, automatable technique which incorporates the method of Dolbeare, et al. to survey dividing cell populations, by the use of one or more halogen-specific monoclonal antibodies which distinguish DNA replication of cell sub-populations when labeled in vivo or in vitro.

The monoclonal antibodies which can discriminate between nucleoside analogs which bear different halogen provides a means to monitor the incorporation of several DNA precursors into any of several sub-populations in the same cell preparation. When these additional specific nucleoside precursor markers are used in the flow cytometric measuring technique of Dolbeare et al., it is possible to measure DNA synthesis in two or more sub-populations of cells at one time Each particular halogen nucleoside analog can be identified by an independent labeled halogen-specific monoclonal antibody and surveyed coincidentally with the total DNA of the cells. It is also possible to measure two different aspects of proliferation in the same population (e.g. total cell cycle time and fraction of cells in S-phase).

DETAILED DESCRIPTION OF THE INVENTION

The present invention describes monoclonal antibodies which have specific affinity for halogenated nucleoside analogs which carry a particular halogen, the hybrid cell lines which continuously produce these antibodies and the method for making such hybridomas. These antibodies may be used in a method for the detection of cell proliferation activity of multiple cell populations by measurement of the incorporation of each of the independently identified nucleoside analogs into individual cells by cytometric methods or into cell populations by the flow cytometric method of Dolbeare, et al (U.S. Pat No. 4,812,394)

The subject invention provides monoclonal antibodies with sufficient differential specificity for the halogen moiety of the halogenated nucleoside analog which is incorporated into DNA, that flow cytometry analysis of DNA incorporation may be performed with identification of more than on incorporated halogenated nucleoside analog. Incorporation of more than one labeled nucleoside analog enables concurrent sampling analysis of more than one subpopulation and evaluation at more than one set time point.

Use of these new halogen-specific nucleoside analog monoclonal antibodies avoids the problems of currently available monoclonal antibodies which do not have sufficient specificity for the halogen moiety of the nucleoside precursor that they can adequately distinguish the labeling of a first cell sub-population from labeling of additional sub-populations, that are labeled at a different time, with nucleoside analogs that contain different halogen molecules. The halogen-specific monoclonal antibodies of the subject invention may be used in a cell kinetic labeling method which is as efficient as labeling by multiple radioisotopes, such as with $^3$H-thymidine and $^{14}$C-thymidine, but which does not present radioactivity safety concerns for in vivo labeling. Because specific monoclonal antibodies which bind to a nucleoside analog bearing a particular halogen have not previously been available, such a non-radioactive multiple labeling approach has not heretofore been possible.

Monoclonal Antibodies

Accordingly, several cell lines were developed which secrete monoclonal antibodies which will react specifically with nucleoside analogs which contain a particular halogen. Hybridoma cell lines were developed which produce highly specific monoclonal antibodies which bind to and identify the presence of halogenated deoxyuridines, but with a distinguishable preferential affinity for a particular halogen. In the representative described example, the monoclonal antibody disclosed shows a preference for the brominated over the iodinated analog.

Development of antibodies to small organic molecules is achieved by initial linkage of the small molecule to a carrier protein, which provides a complex which the immune reactive cells can recognize as an antigenic determinant site. The small molecule, or a derivative of it is termed a hapten and is linked to a carrier molecule. This so-called hapten-protein complex induces the immunoreactive cell to form antibodies to (1) the various linker sites on the molecule, (2) the carrier protein, (3) the hapten, (4) the hapten carrier-protein complex, or (5) any combination of the hapten, the linkage chemistry and the carrier protein. Although the specific reactive site is not well defined, the site and chemistry of the hapten conjugation to the carrier molecule appears to influence the specificity of the antibodies produced even when the molecules differ by as little as one atom. This invention utilizes the ability of the immune reactive cells to recognize and distinguish molecules which differ by the halogen molecule, and produce specific monoclonal antibodies to a nucleoside analog with a specific halogen.

Tolerization to Halogens

Monoclonal antibodies are made which are capable of distinguishing the presence of an incorporated halogenated nucleoside analog, in the presence of another nucleoside analog which carries a different halogen atom. The monoclonal antibodies of the invention are produced in animals which ar preliminarily tolerized to the second halogenated nucleoside. The tolerization procedure is a method whereby the immunogenic reactive specificity for a compound is improved by prior injection of sub-immunogenic doses of a related tolerization compound. The tolerization compound is a non-metabolizable compound which contains a different halogen in the nucleoside than the compound used for the immunization. Tolerization compounds may be, but are not limited to, polymers which are non-metabolizable or non-physiological mixtures of right and left-handed stereoisomers of amino acid chains, or compounds in which metabolism is inhibited by glycosylation, or compounds containing unnatural amino acids. The long polymers of the tolerizing compounds could be a few hundreds of amino acids in length, but are different in character from the very large carrier proteins, in the range of 800,000 M.W., such as KLH, which are used as immunization carrier proteins In the modified immunization method of this invention, animals of a nucleotide-sensitive species are given a preliminary tolerization to a halogenated nucleoside analog by injection with a dose of second halogenated nucleoside analog which has been conjugated to a non-metabolizable polymer. Animals are subsequently immunized with a nucleoside analog hapten which bears the first halogen molecule.

The halogens used in the tolerization agent and the immunization agent are selected from the group comprising bromine, iodine, fluorine and chlorine, where different halogen molecules are used for the tolerization and immunization compounds. A preferred method of tolerization includes injecting an animal species, which is unusually sensitive to immunizations with nucleotides, preferably SJL/Jax mice, with halodeoxyuridine monophosphate, including, but not limited to BrdUMP, IdUMP, FldUMP and CldUMP, which has been conjugated to a non-metabolizable polymer, including, but not limited to a polymer of D-amino acids. Tolerization may be with 10 to 200 ug of halogenated nucleoside analog, which has been conjugated to a non-metabolizable polymer of D-amino acids. In the preferred mode, tolerization injections to the SJL/Jax mice are 100 ug of iododeoxyuridine monophosphate conjugated to a polymer of D-glycine-D-lysine (IdUMP-DGL), which are given in two injections at three month intervals.

Immunization of Animals

Monoclonal antibodies which react with a specific halogen are produced by immunization of a tolerized first species of an animal, with an antigen which contains a halogenated nucleoside. The halogenated nucleotide of the hapten including, but not limited to BrdUMP, IdUMP, FldUMP and CldUMP, may contain a different halogen than that halogen on the non-metabolizable compound that is used for the tolerization procedure. The nucleic acid analog hapten for immunization is conjugated to a carrier protein, which may be selected from a group of suitable carrier proteins, which include, but are not limited to keyhole limpet hemocyanin (KLH), serum albumins, globulins and the like. Keyhole limpet hemocyanin (KLH) is conveniently used in the subject invention. Antibodies are induced by repeated administration (i.p.) to the animal of a suitable amount of the antigen-carrier protein conjugate, generally between about 10 ug to about 200 ug, preferably about 100 ug of antigen-carrier protein conjugate mixed 1:1 with RIBI Adjuvant, per animal, per administation, at intervals of about two weeks for three immunizations.

Fusion of Hybridomas

Immunosensitized spleen cells or lymphocytes, preferably sensitized spleen cells, which are thus capable of producing antibodies to the immunizing antigen, are removed from the animal and fused to immortally reproducing cells, preferably myeloma cells of the first species of animal or of another animal species, to produce hybrid cells. The hybrid cells so produced are cultured and isolated clones of the hybrid cells, which are termed hybridomas, which continuously secrete monoclonal antibodies which react with nucleoside analogs bearing the specific halogen of the immunizing antigen are selected by a direct-binding ELISA assay of Stanker et al. (1986) (*J. Immunol.* 136: 4174–4180). Hybridomas are cultured to generate quantities of these monoclonal antibodies, which may be used in the form of hybridoma supernatant, or as ascites fluid, or they may be isolated and purified, if necessary. These monoclonal antibodies ma be used for assay of samples for the presence of halogenated nucleoside analogs which contain a particular halogen.

The hybridomas may be propagated in a suitable host animal or grown in a suitable culture or carrier medium. Host animals include but are not limited to mice, rats, hamsters, guinea pigs, rabbits and the like. Suitable culture or carrier media include, but are not limited to, ascites fluid and hybridoma supernatant, other than one of the culture media specified above.

The monoclonal antibodies specific for brominated nucleoside analogs are given the same names as the cell lines from which they are derived, that is Br-1, Br-3 and Br-5, respectively. Samples of these cell lines are deposited with the American Type Culture Collection (ATCC), 12301 Parklawn Drive, Rockville, Md. 20852, USA with Accession No. HB10699, HB10700 and HB10698.

Staining of DNA

The immunochemical stains for identification of nucleoside analogs comprise an anti-analog antibody, which is an antibody raised against each of the halogenated nucleoside analogs, and a labeling means for generating a signal. Each anti-analog antibody raised against a halogenated nucleoside analog is screened for its specificity for an individual halogen. Those which have sufficient discrimination between different halogens are selected and labeled by any of several means including, but not limited to, direct labels, indirect labels and sandwich-type labels. Labels ma be detected by spectrophotometric, fluorometric, radioactive or electron opacity means. Preferably, fluorescent signals are used. Fluorescent dyes selected for the signals may be from the group comprising, but not limited to fluorescein, Texas Red (a trade name product of Molecular Probes, Inc., Junction City, OR), tetramethylrhodamine or phycoerythrin. Signals may determined directly or be assayed indirectly by further amplification with an enzyme-immunoreaction assay including but not limited to a biotin-avidin amplification system.

The stain specific for the total, undenatured DNA, is a DNA specific fluorescent dye. The dye may be nonintercalating, including, but not limited to Hoechst 33342 and Hoechst 33258, mithramycin, chromamycin $A_3$, olivomycin, 4'-6-diamidino-2-phenylindole, and the like; or it may be an intercalating fluorescent dye including, but not limited to, the group consisting of ethidium bromide, propidium iodide and acridine orange, and the like. Selection of the dye must include considerations that possible loss of stoichiometry can occur in the binding of the second stain to the total DNA, depending upon the DNA denaturation method.

Use of Halogen-Specific Nucleotide Selective Monoclonal Antibodies for Flow Cytometry The present invention provides a method for distinguishing DNA synthetic activity in more than one site. DNA synthesis in different cells or cell sub-populations can be monitored by tracking the incorporation of more than one particular halogenated nucleoside analog. In the flow cytometric measurement procedure of Dolbeare, et al,(U.S. Pat. No. 4,812,394), which is incorporated by reference, incorporation of nucleoside can be measured in a sub-population concurrently with the total DNA in order to quantify the time and degree of DNA synthesis. The availability of immunochemical reagents which permit detection of nucleoside analog incorporation of more than one halogen moiety, permit tracking of DNA precursors with different halogenated nucleoside analogs which can be added in sequence.

Characterization of the presence and distribution of particular halogenated nucleoside analogs, by assay with halogen-specific nucleoside analog monoclonal antibodies would permit, rapid, automatable analysis of the temporal relationships of DNA analog incorporation in cell proliferation studies.

The halogen-specific nucleoside analog reactive immunochemical reagents produced by the described method can be used in a non-radioactive method for monitoring the proliferative states of several cell populations. Added pulses of each halogenated nucleoside analog, which are incorporated during the DNA synthetic stage of a cell subpopulation can be tracked by observing binding through the various stages of the cell cycle. Small populations of replicating cells can be identified by immunochemical detection of halogenated nucleoside precursors added and sampled at various times during the cell proliferation. The presence of halogen specific immunochemical reagents make possible specific labeling of cell subpopulation DNA replication which previously was not possible with monoclonal antibodies which could not discriminate between nucleoside analogs which differed only by the halogen moiety.

Cells labeled with immunochemical reagents may be examined individually in single cells on slides or they may be evaluated in large quantity in a flow cytometer. For evaluation of nucleotide incorporation with the immunochemical reagent, the double stranded DNA of the cells must be partially denatured to allow the fluorescently-labeled monoclonal antibody to bind to the particular incorporated halogenated precursor. Partial denaturation may be induced by any of several methods, including but not limited to, treatment with mild acid or organic solvents, nuclease enzymes, or with heat treatment. The anti-analog antibody of the immunochemical reagent is bound to the specific halogen of the incorporated nucleoside analog.

When stained with an immunochemical reagent that binds to the halogenated nucleoside analog, and contains a means to generate a fluorescent signal, the fluorescently stained cells can be monitored by flow cytometry. The immunochemical stain may be linked to the antibody by a direct means or indirectly through enzymes which generate fluorescent or colormetric products from colorless substrates. Such techniques are standard preparations in cell biology. If desired, the detection of the labeled immunochemical stain may be amplified by an enzymatic amplification system such as, but not limited to, covalently linking the anti-analog antibody to one or more biotin molecules and complexing the reaction with avidin molecules. The avidin-biotin amplification of the enzyme endpoint reactions is well known in the development of detectable spectral endpoints in biological assays.

Preparation of Labeled Cell Populations

Cells grown in the presence of a particular halogenated nucleoside analog precursor are labeled by treatment with a halogen specific monoclonal antibody that binds preferentially to that particular halogen. A reagent for each halogen-specific monoclonal antibody for a particular halogen is labeled with a different fluorescent molecule following partial denaturation of the DNA, and a fluorescent marker for the undenatured DNA is also applied to the cells before assaying them in the flow cytometer. Using appropriate wavelengths, the fluorescence of each incorporated halogenated nucleoside analog is plotted versus total DNA of cells. The wavelength of each fluorescent marker is sufficiently distinct to allow for independent measurement of each incorporated nucleoside analog as well as the total DNA content. A non-specific halogen reactive monoclonal antibody may be used in a differencing mode with a specific halogen reactive monoclonal antibody to determine binding of a second halogen molecule.

Halogen-specific Monoclonal Antibodies as Attachment Agents

The specificity of the described monoclonal antibodies of this invention may be utilized as attachment agents in an affinity binding procedure or device for selection of nucleic acid analogs which have the iodinated, brominated, chlorinated or fluorinated moiety. Compounds with these functionalities may reversibly bind specifically to monoclonal antibodies, produced by this invention, which may be fixed to a surface in a column or similar substrate. There are many separation methods to reversibly bind and release halogenated deoxyuridines from the column including but not limited to alteration of the ionic concentration of the column. Differential binding of halogenated nucleic acid analog compounds to the fixed monoclonal antibody in a column may be used to concentrate or purify these compounds.

The following examples, presented by way of illustration, serve to explain the present invention in detail.

These examples are not to be construed as limiting the invention to the precise forms or modes disclosed. In fact, several improvements and modifications are possible. It is intended that such improvements and modifications are encompassed by the appended claims.

EXAMPLES

1. Tolerization of Animals to Halodeoxyuridine

To improve the selection of antibodies which have significantly greater reactivity to one halogenated nucleic acid analog in preference to analogs which contained other halogens, animals of a species known to be nucleotide sensitive were pretreated with a halogenated nucleic acid analog, prior to immunization with a hapten containing a different halogen atom. SJL/Jax strain of mice, which are known to be sensitive to immunizations with nucleotides, were selected and injected with a tolerization dose of halogenated nucleoside analog conjugated to an amino acid polymer. In the preferred example, the SJL/Jax mice were tolerized to iododeoxyuridine conjugated to a non-metabolizable amino acid polymer. Animals were given 10–200 micrograms of conjugated halogenated nucleoside per dose, in the preferred mode, two 100 microgram doses of iododeoxyuridine nucleoside polymer conjugate, given three months apart. The tolerization nucleoside was iododeoxyuridine monophosphate conjugated to the D-amino acid polymer, D-glycine-D-lysine (IdUMP-DGL) by the method of Erlanger, et al. PNAS 52: 68–74 (1964).

2. Immunization of Animals with Antigen

To effectively immunize animals to halogenated nucleoside analogs the small nucleoside molecules were linked to an immunogenic protein carrier. In the preferred mode, the hapten-protein carrier complex used for immunization was produced by conjugation of bromodeoxyuridine monophosphate to keyhole limpet hemocyanin (KLH) to form (BrdUMP-KLH) using the mixed anhydride method of Erlanger, et al 1959 (J. Biol. Chem. 234:1090–4). By this procedure, an intermediate is formed which readily couples to the free amine groups of the protein. KLH conjugates of bromodeoxyuridine monophosphate (BrdUMP KLH) were used for immunization and BSA conjugates of bromodeoxyuridine monophosphate (BrdUMP-BSA) were used for ELISA screening of hybridoma clones. In the preferred mode, three injections of 100 ug of BrdUMP-KLH in RIBI adjuvant were administered intraperitoneally to the nucleotide sensitive mice during the period between the tolerizing injections of IdUMP-DGL.

3. Production of Hybridomas

Prior to removal of immunized cells for fusion with immortalized cells, the immunogen titer was increased by an additional booster injection of immunogen to the tolerized mouse. In particular, four days prior to lymphocyte fusion, the immunized mouse hapten-specific serum titer was boosted with an intrasplenic injection of 100 ug BrdUMP-KLH conjugate in sterile saline. Spleen cells were removed and fused to SP2/0 myeloma cells by standard methods (see Bigbee, W. L. et al Molecular Immunology 20: 1353-1362 (1983)), and grown under the conditions described by Stanker, et al (1986)(J. Immunol. 136: 615–622). Fusion is not limited to the use of SP2/0 myeloma cells and the use of other immortally reproducing cells is contemplated to be within the scope of this invention.

Following fusion, hybridomas were screened in a direct binding ELISA method, as modified by Stanker (J. Immunol 136: 615–622) for the ability of the antibodies to recognize the appropriate BrdUMP-BSA conjugates.

4. Characterization of Antibodies by ELISA Assays

Antibodies in the culture fluids of growing hybridomas were screened for their binding affinity to halogenated deoxyuridines incorporated into DNA. In the preferred example, screening was by the direct binding ELISA method of Vanderlaan, M., et al. (1986) Cytometry 7: 499–507) which was modified as follows:

The 96-well Immulon-II microliter plates (Dynatech Laboratories, Alexandria, Va.) were coated with single stranded 10% substituted BrdUMP-DNA (0.2 ug per well) by drying overnight, and then incubated for 1 hour at 37° C. with the hybridoma supernatants. The plates were carefully washed with a solution of 0.05% Tween-20 in water. Peroxidase, conjugated with goat anti-mouse antiserum, (United States Biochemicals, Cleveland, Ohio) diluted 1:500 in assay buffer (0.1 M Tris, 0.075 N NaCl, 0.001% Tween-20, pH 7.6) was added to each well. Following a second 1 hour incubation at 37 ° C., the plates were washed again and the substrate, 2,2 amino-di-3-ethylbenzthiazoline sulfonic acid (ABTS), added. Absorbance measurements at 405 nm were taken as a function of time and the resulting data were transferred to a Macintosh computer and subsequently analyzed using the "Cyberdoma" ELISA software described by Slezak, et al (1983)(J. Immunol Methods 65: 83–95). Hybridoma cells from wells showing a positive response in the ELISA screen were expanded and subcloned twice by limiting dilution to insure their monoclonal origin. Ascites fluid was prepared in irradiated mice according to Stanker, et al (1986) (J. Immunol. Methods 136: 615–622) and the monoclonal antibodies purified from the ascites by hydroxylapatite chromatography (Stanker et al (1985) J. Immunol. Methods 76: 157–169).

Hybridomas from the fusions were cultured in 30, 96-well microculture dishes. Cells secreting antibodies that recognized BrdU-DNA were expanded and re-screened in the same ELISA assay against denatured DNA and denatured IdU-DNA. Only those clones secreting antibodies reacting selectively with BrdU-DNA were saturated, expanded and further characterized. Three antibodies of desired specificity were identified and were named Br-1, Br-3, and Br-5. These antibodies, which were all derived from one mouse, were subcloned twice by limiting dilution and large quantities frozen for storage.

Isotypes of the monoclonal antibodies were determined by direct-binding ELISA with isotype-specific antisera (Southern Biotech, Mobile, Ala.). All three antibodies were determined to be IgG1 antibodies with kappa light chains.

5. Specificity of Monoclonal Antibodies

A competition enzyme-linked immunosorbent assay (c-ELISA) wa developed to assess the specificity of the antibody for halogenated deoxyuridines by the method of Stanker, et al. (1986) described previously. The competition ELISA data was normalized using 100% activity as the optical density in wells in which antibody was bound to the solid phase antigen (BSA-hapten) in the absence of any competitor. The test wells, each containing different amounts of competitor, were normalized to the 100% activity wells. Percent inhibition was calculated by subtracting the normalized percent binding activity from 100. A smaller $I_{50}$ value indicates a higher relative affinity of the antibody for the compound. $I_{50}$ values were estimated graphically from competition ELISA data. When 50% inhibition could not be attained, the value of the highest level of competitor tested is reported. Competition binding data for antibodies reactive with brominated nucleoside analogs are shown in FIG. 1, and the values represent the averages from at least 12 independent assays.

Figure 1:
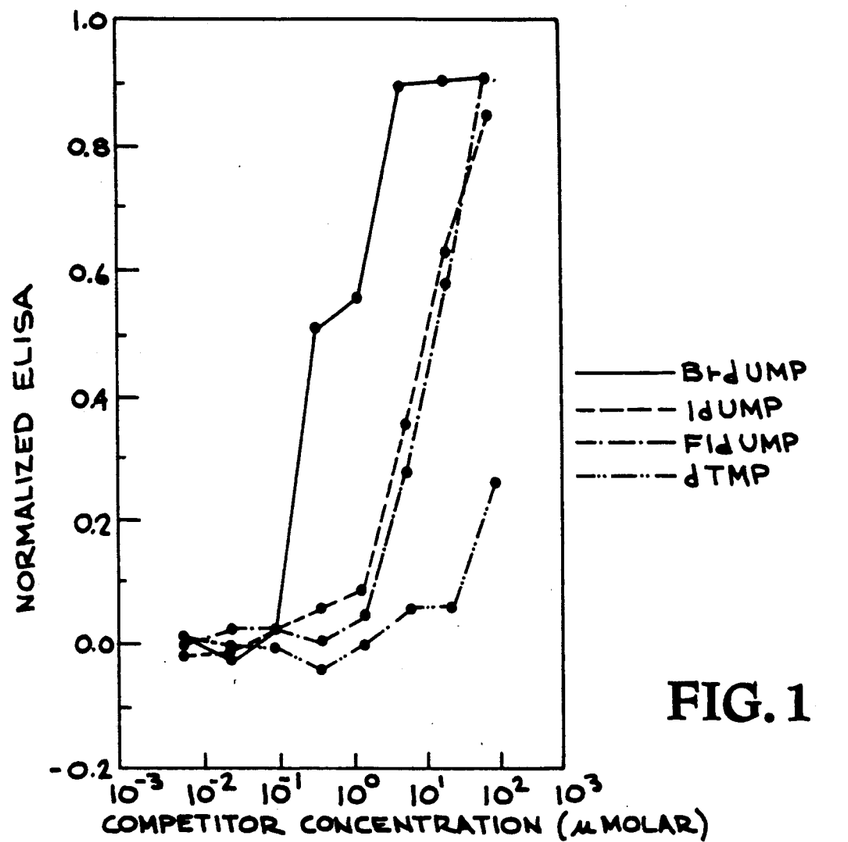
FIG. 1—Competition Binding Data for Monoclonal Antibodies Reactive to Halogenated Nucleotide Analogs.

The binding of the antibody Br-3 to each of several halogenated deoxyuridines was compared and is shown in FIG. 1. The concentration of IdUMP which causes a 50% binding inhibition to monoclonal antibody Br-3 is 100 times greater for IdUMP than with BrdUMP. The Br-3 binding of the fluorinated deoxyuridine analog is comparable to that of the iodinated analog. The Br-3 monoclonal antibody is specific for the deoxyuridines, as concentrations of thymidine monophosphate (dTMP) of up to $10^2$ micromolar did not produce even 50% binding inhibition.

Figure 2:
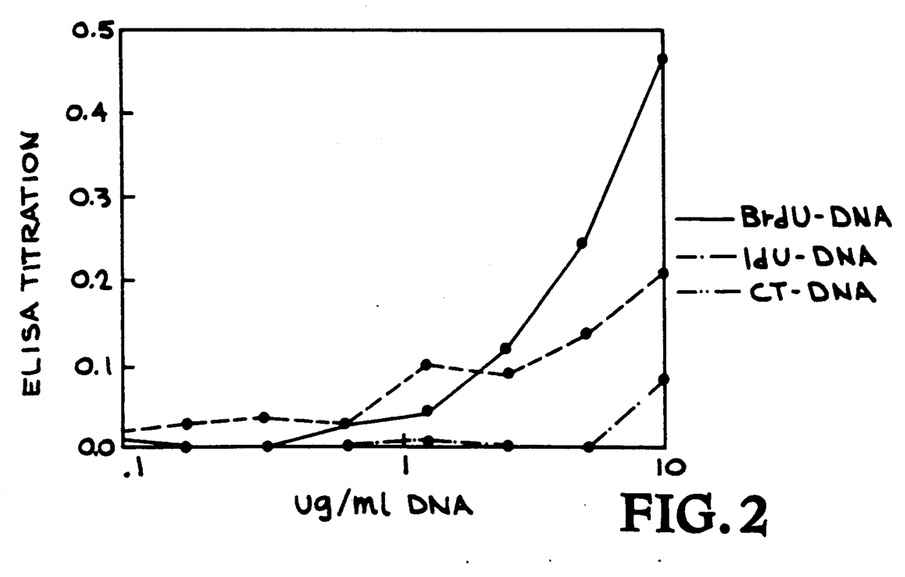
FIG. 2—Binding Capacity of Br-3 to Immobilized Halogen Substituted DNAs.

Binding of Br-3 to immobilized DNA was demonstrated in FIG. 2, which shows the binding to BrdU-DNA, IdU-DNA and CT-DNA.

6. Activity of Monoclonal Antibodies Conjugated to Fluorescent Dyes

Br-3 can be conjugated to a variety of fluorescent dyes with complete retention of specific antibody activity. Samples of Br-3 were conjugated by the method of Rinderknecht, H. *Experientia* 16: 430 (1960), to fluorescein isothiocyanate (FITC), a green fluorescent dye, with full retention of the selectivity of the antibody.

As proof of the antibody function during multiple dye labeling, CHO (Chinese Hamster ovary) cells were grown in the presence of IdU and fixed and stained with IU-4 antibody ( Vanderlaan, et al, (1986)). This antibody, when used with FITC-goat-anti-mouse antibody, has a specificity for IdU of 0.5 uMolar.

Samples of Br-3 antibody were conjugated to the blue fluorescent dye, 7-amino-4-methylcoumarin (AMCA), which is excited maximally at 345 nm and emits maximally at 445 nm, by the method of Khalfan, H., et al., Biochemical J. 18: 497-99 (1986). Antibody activity remained after conjugation and the AMCA could be detected along with the propidium iodide staining of the total DNA by two color labeling in a dual laser flow cytometry system.

To demonstrate the specificity of identification of the fluorescent labeling in the flow cytometry system, cells were grown in the presence of BrdUMP and stained with Br-3 antibody and goat-anti-mouse AMCA and mixed with other cells independently grown in the presence of IdU and stained with the IU-4 antibody and goat-anti-mouse FITC. Following a 30 minute growth period, in presence of the halogenated pyrimidines, the cells were fixed, stained and analyzed according to the method of Dolbeare (U.S. Pat. No. 4,812,394). The cells were independently analyzed for each halogen specific monoclonal antibody stain, and propidium iodide fluorescence was monitored as the base line of unaltered DNA content. Monoclonal antibody binding analysis for each labeled immunochemical reagent was done in a dual laser flow cytometer. In flow cytometry analysis, the FITC fluorescence is plotted as the log of the IdU content on the Y-axis while propidium iodide fluorescence, representative of DNA content, is plotted on the X-axis. Analysis by list mode data collection demonstrates the presence of cells in the BrdU growth medium which are in G1, G2 and S phase, as well as cells unstained with FITC.

Flow cytometry analysis of cells which have recently incorporated BrdU indicated by AMCA labeling, reported on the Y-axis, is plotted against propidium iodide labeling which is representative of total DNA on the X-axis. The G1 and G2 stage cells which did not undergo active replication can be identified.

7. Method for Labeling of Cell Populations with Specific Antibodies

Multiple labeling of replicating cells in which immunochemical stains are used with antibodies specific for bromine and iodine, can be made by growing cells separately with each precursor. Cells are grown in a physiological environment with different halogenated nucleoside analogs added at different times. The physiological environment could be in vivo, or in cell cultures or as free cells in suspension. Monoclonal antibodies which react specifically with one or more different halogens may be labeled with various fluoresceinated dyes for detection following excitation by appropriate lasers. Optical detectors suitable for the wavelength emitted from each fluorescent dye quantitate the cells which have incorporated DNA precursors. The unreacted portion of the DNA is detected by measurement of the emission spectra of a chelating fluorescent dye which binds to double-stranded DNA.

Figure 3:
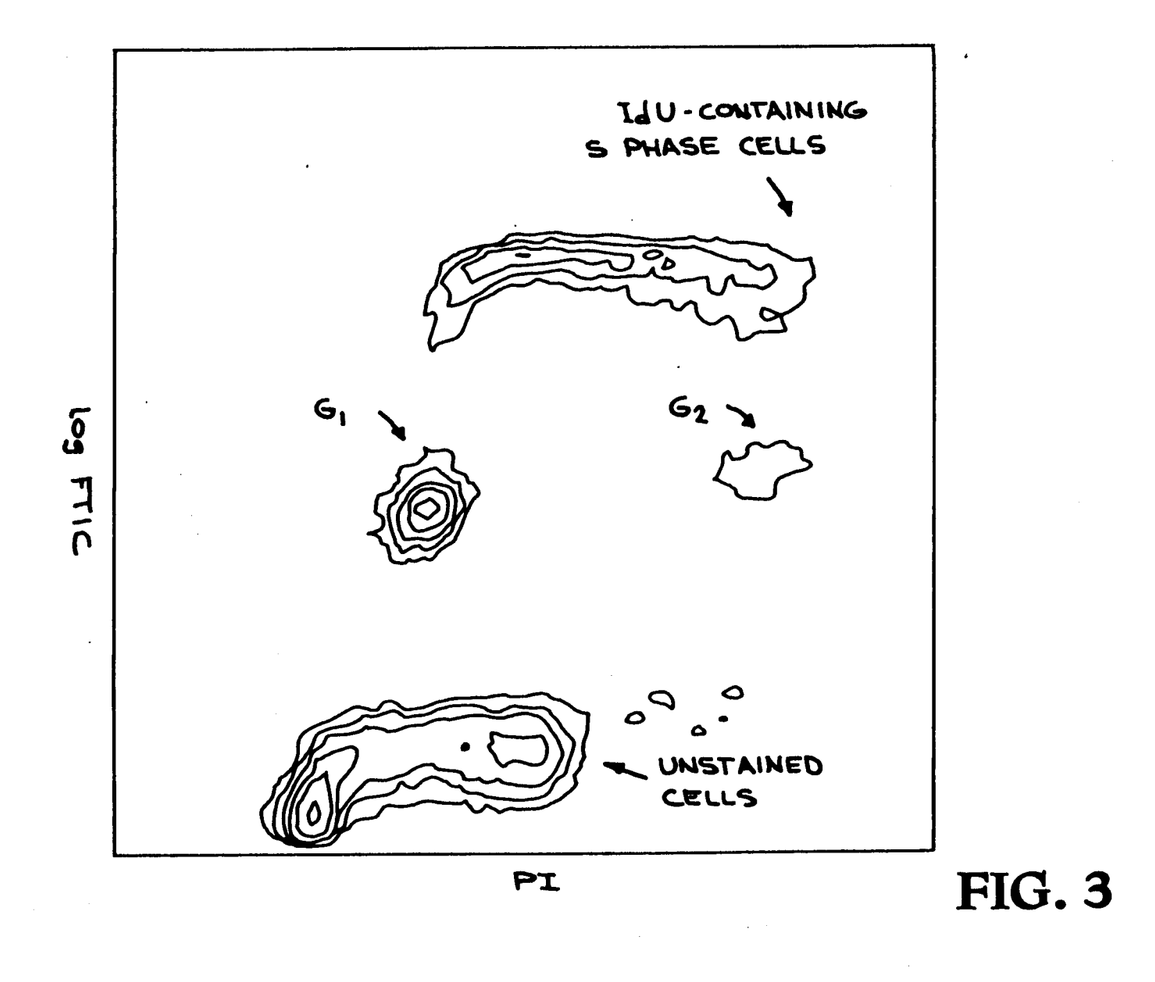
FIG. 3—IU-4 Binding of CHO Cells Grown with IdU. IdU content of cells indicated by FITC fluorescent IU-4 antibody binding (Y-axis) is plotted against total DNA content as indicated by PI fluorescence (X-axis).
Figure 4:
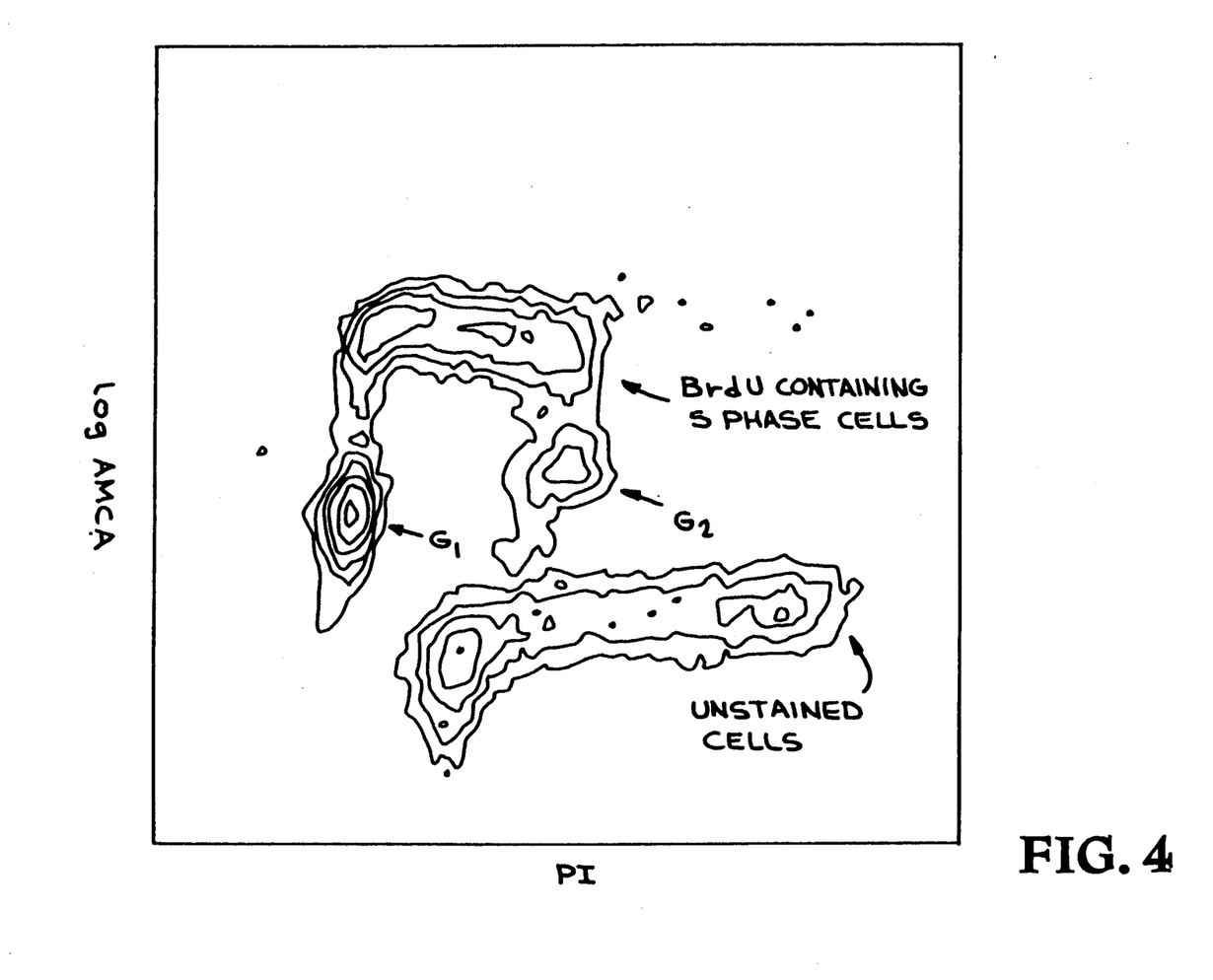
FIG. 4—Br-3 Binding of CHO Cells Grown with BrdU. BrdU content of cells indicated by AMAC fluorescent Br-3 antibody binding (Y-axis) is plotted against total DNA content as indicated by PI fluorescence (X-axis).
Figure 5:
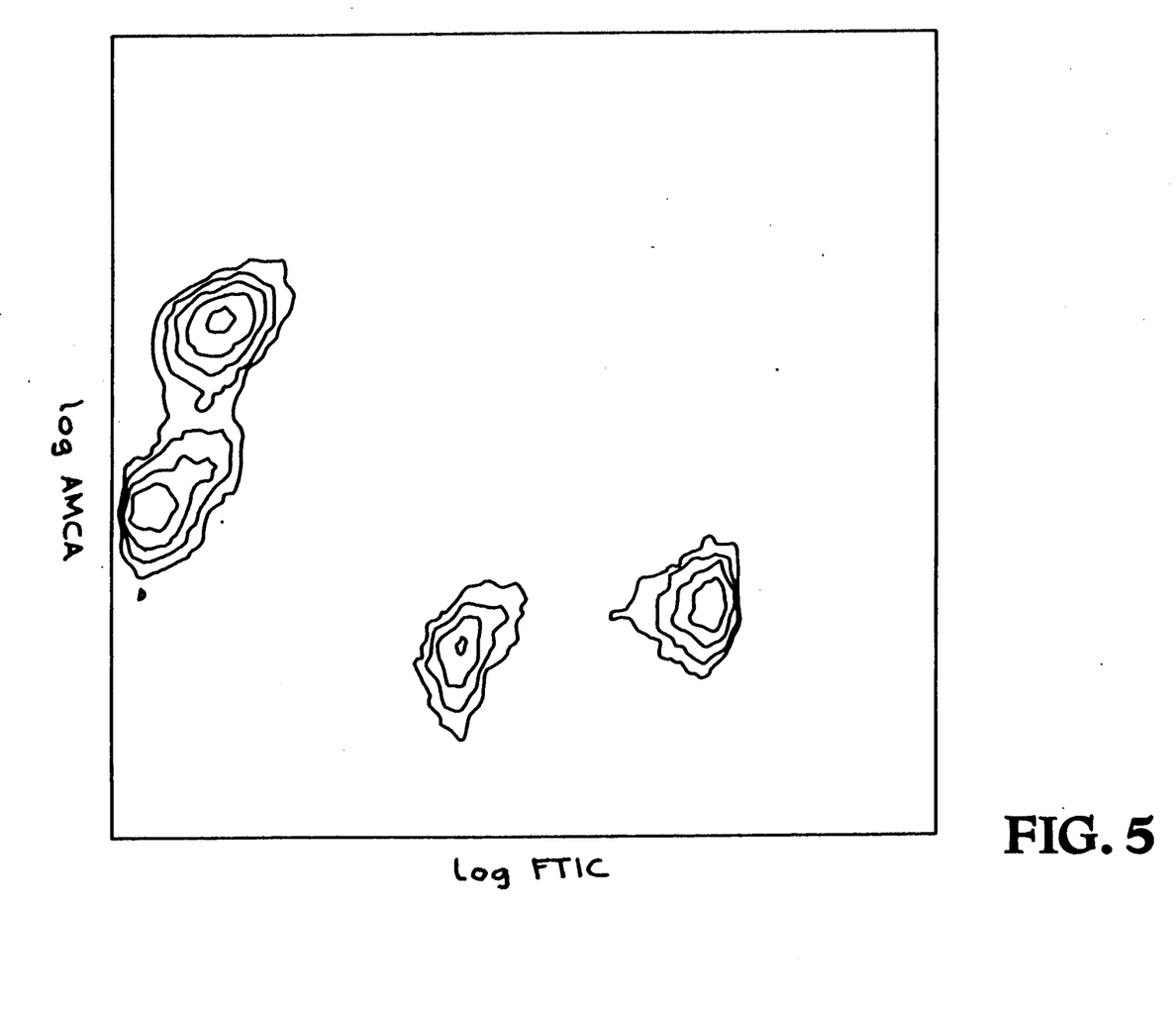
FIG. 5—Difference Plot of Fluorescent Labeling with Br-3 and IU-4 Antibodies in Cells Mixed After Growth Individually in the Presence of Either IdU or BrdU. BrdU is labeled with Br-3 coupled to AMAC fluorescent marker (Y-axis) and IdU is labeled with IU-4 coupled to FITC fluorescent marker (X-axis).
Figure 6A:
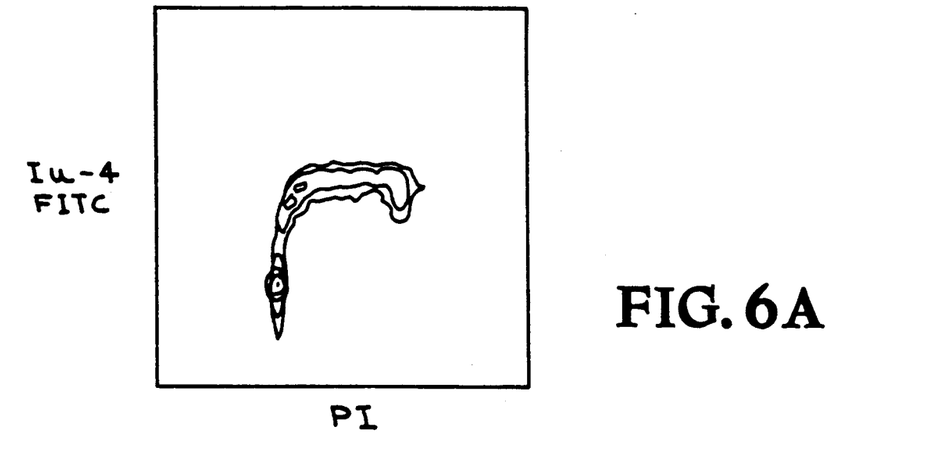
FIG. 6—Two Parameter Flow Histograms Showing Proliferation of CHO Cells by Detectable Incorporation of BrdU in the Presence of IdU Incorporation. Cells were grown in the presence of IdU for 2,6 or 24 hours and stained with FITC conjugated IU-4 antibody (Panel 6 A,C,E) or FITC conjugated Br-3 antibody (Panel 6 B,D,F). Cells of the 24-hour IdU incubation samples were given an additional 30 min. exposure to BrdU prior to sampling.
Figure 6B:
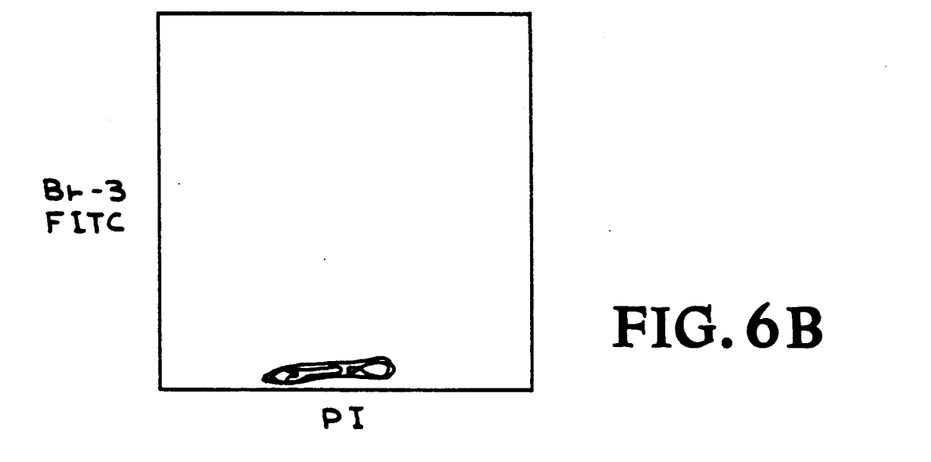
Figure 6C:
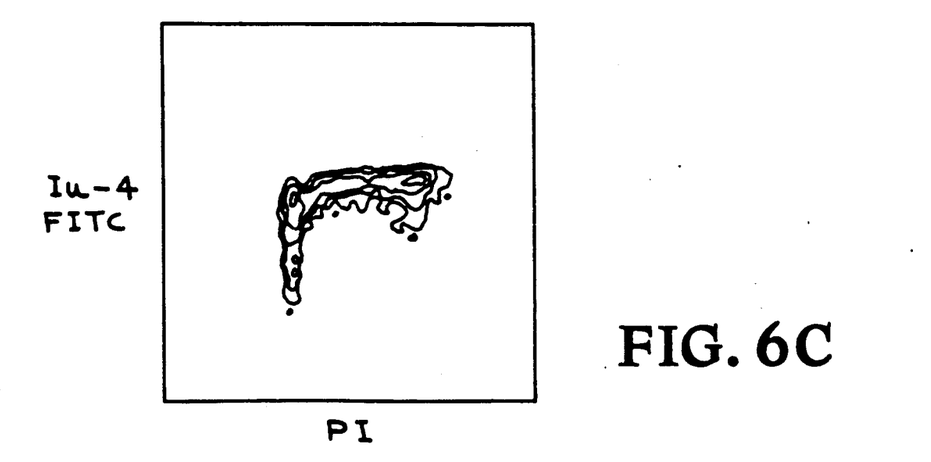
Figure 6D:
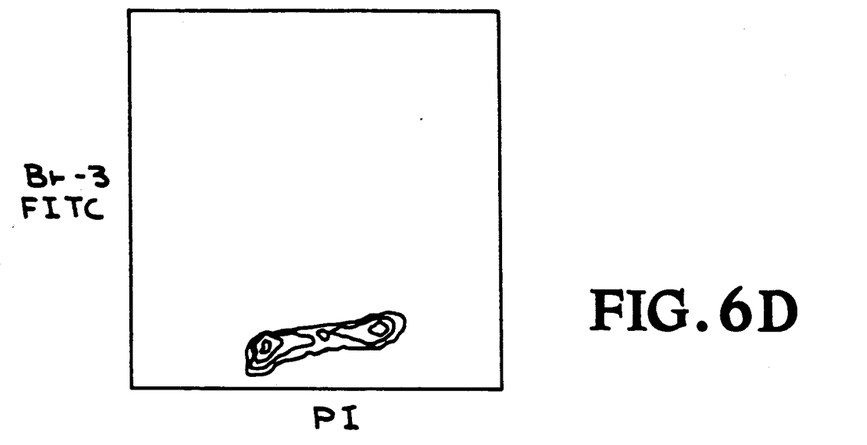
Figure 6E:
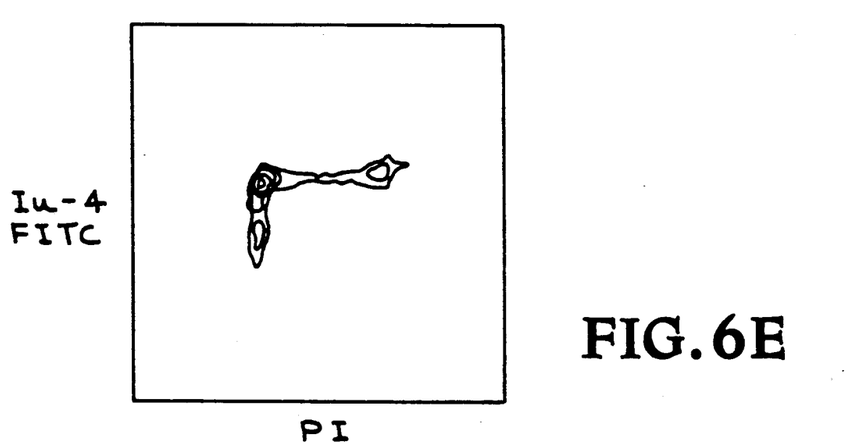
Figure 6F:
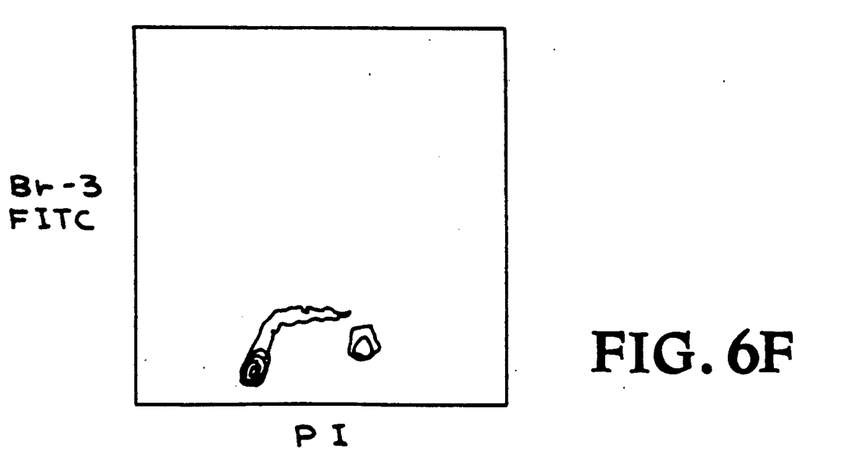

The ability to use immunochemical reagents for two detectable halogen-specific labels is shown in FIGS. 3-5. Cells were labeled by growing for 30 minutes in the presence of halogenated pyrimidines, fixed and stained by the standard protocols described by Dolbeare. CHO cells, which were grown in the presence of IdU were fixed and stained with the halogen-specific monoclonal antibody IU-4 which was conjugated to FITC-goat-anti-mouse antibody. In a separate flask, cells were grown in the presence of BrdU and stained with bromine-specific monoclonal antibody Br-3 which was conjugated to AMCA goat-anti-mouse antibody. The independently stained cells were then mixed stained with propidium iodide and analyzed by flow cytometry. FIG. 3 shows a histogram of the standard analysis method with FITC fluorescence representing the log of the IdU content (Y-axis) plotted against the PI fluorescence representing the total DNA content (X-axis). The location of $G_1$, $G_2$ and S-phase cells is marked, as well as cells that were not stained with the FITC-stained antibody, probably those from the BrdU culture. FIG. 4 shows the similar staining pattern where the halogen-specific staining is that for the AMCA labeled cells which incorporated the BrdU nucleoside analog (Y-axis). In FIG. 5 the fluorescence of the two halogen-specific immunochemical stains are plotted against each other, a graphic demonstration that there are unstained cells and cells which react only to each fluorophore in the preparation. The stained cells are those which were in S-phase (DNA synthesis phase) during the incubation with either halogen containing nucleoside analog, and the unstained cells are those which were in a non-synthetic stage, $G_1$ or $G_2$. These figures demonstrate that the three fluorophores used are sufficiently spectrally distinct that independent measurement is possible. The incorporation pattern of two pyrimidine analogs can be measured at the same time because the relative strength of the BrdU and IdU staining is comparable.

8. Assay of Cell Replication Activity in a Mixed Population of Cells

Antibodies produced by the above method can be used to make immunochemical stains for identification of various populations of cells which are present in tissue or a cell suspension. Immunochemical reagents which contain different halogen specific monoclonal antibodies are applied to a replicating cell population, which has been pulse labeled with halogenated nucleoside analogs, to distinguish the fraction of the population which are undergoing proliferation. Identification of DNA replication may be done concurrently with the addition of drugs which alter cell replication, in order to monitor the intensity, time and duration of the drug action.

The data herein presented indicate that the monoclonal antibodies described are suitable for detection of a nucleoside analog which contains a particular halogen moiety. When these immunochemical agents are administered to a mixture of dividing cells at different times during the growth period, measurement of each of these halogen-specific markers allows determination of the growth fraction of that cell sub-population in the mixed population. Multiple labeling, allows assessment with fewer sampling periods and without the use of radiolabeled nucleotide precursors.

In a preferred example, flow cytometric analysis was performed on CHO AA8 cells which had been grown in the presence of IdU and/or BrdU. Two parameters were analyzed, indicating the incorporation of brominated or iodinated deoxyuridine and the total DNA. The cells were grown overnight in the presence of 5 uM IdU, and were harvested at 2, 4, 6 and 24 hours later. In a second flask, cells which had grown in the presence of 5 uM IdU overnight were washed and grown for an additional period of 30 minutes in the presence of 5 uM BrdU. Each sample of the incubated cells were washed twice with PBS-7 (Phosphate buffered saline: 0.075 mM NaCl, 0.1 M Na$_2$HPO$_4$ and NaH$_2$PO$_4$; pH 7.0), removed from the flask wall with trypsin and washed twice again with PBS-7 prior to fixation with 50% of EtOH at 0° C. Cell samples from each time point were assayed for specific halogen incorporation and the total DNA by the method of Dolbeare, et al. In each sample, DNA was denatured and the cells were stained with either IU-4 or Br-3 antibody stain conjugated to FITC and propidium iodide. Monoclonal antibody binding was determined with the use of FITC-conjugated anti-mouse immunoglobin in a dual-beam flow cytometer with an excitation laser at 488 nm (2 W power) and the emitted fluorescence sampled with a 514 nm band pass filter and differential log amplifier. The DNA content was determined from propidium iodide fluorescence (emission maximum 630 nm) using a 600 nm long pass filter and a linear amplifier. The data from these signals was used to form a bivariate 64×64 channel distribution with the population of cells identified by DNA content along the x-axis and the log of the halogenated deoxyuridine fluorescence on the y-axis.

Labeling of cells on two-parameter histograms is shown on FIG. 6A-F. Those cells which were labeled continuously with IdU for 2, 6 and 24 hours are stained with FITC conjugated to IU-4.(Panels A,C, and E respectively). Initially only the S-phase cells show incorporation of IdU, however as the cells continue to grow, they continue to incorporate IdU until all of the cells are labeled. The culture that was additionally pulse labeled with BrdU at 30 minutes prior to the 24 hour sampling point is shown in FIG. 6-E. Cells labeled with Br-3 are represented by the labeling patterns in panels B, D and F. The 30 minute pulse of BrdU given at the 24 hour period gave a histogram (FIG. 6-F), when stained with a FITC BrdU-specific stain which is similar to that of the IdU labeling in Panel A. There is no staining of cells with BrdU-specific stain at 2 and 6 hour sampling times (FIGS. 6-B and 6-D). These results indicate that an extended period of IdU incorporation did not interfere with the ability of the Br-3 antibody to recognize incorporated BrdU.

Three-parameter measurements were made to illustrate simultaneous labeling of bromodeoxyuridine, iododeoxyuridine and total DNA content. In a preferred example, CHO AA8 cells were grown for 30 minutes in the presence of 10 uM BrdU, washed once with culture media, and grown for an additional four hours in normal media, without nucleoside analog. An aliquot of iododeoxyuridine was added to bring the media concentration to 1 uM IdU, the cells were incubated for 30 minutes and harvested, washed and fixed in ethanol as described above.

For these studies, the Br-3 monoclonal antibody was conjugated to the fluorescent dye 7-amino-4-methylcoumarin-3-acetic acid (AMCA)(BioCarb Chemicals) with the method of Khalfan, et al., described previously. The dye conjugation was accomplished by reacting 10 mg of Br-3 antibody with 52 ug of AMCA N-hydroxysuccinimide ester dissolved in 5 ul DMSO and 2 ml 0.05 M borate buffer (pH 8.5) with 0.1 M NaCl. After reaction for two hours at room temperature, the conjugate was filtered through 0.2 micron filter and dialyzed overnight against phosphate buffered saline (pH 7.2). Any unbound AMCA was removed by passage through a G-25 Sephadex column (Pharmacia LKB, Piscataway, N.J.) in phosphate buffered saline (pH 7.2).

The antibody staining of the cells for detection of incorporated halogenated nucleoside analogs included the following steps: The cells were incubated with AMCA-Br-3 for 30 minutes, then unlabeled goat anti-mouse Br-3 for 30 minutes, and finally with the halogen-specific monoclonal antibody conjugate, FITC-B44 (Becton Dickinson, Mountain View, Calif.) for 30 minutes. The inclusion of a step for incubation of unlabeled anti-mouse antibodies with AMCA-Br-3 stained cells seemed to stabilize the staining.

For assessment of the fluorescent immunochemical stains, a 1 W UV laser, with an excitation wavelength of 351–364 nm was added to the flow cytometry configuration described above. The AMCA dye has an excitation wavelength of 545nm and an emission maximum at 445 nm. Blue fluorescence was collected with a 457 nm band pass filter, and the signal amplified with a logarithmic amplifier. Analysis of the bivariate distributions could be selected for plots of the DNA content versus either of the antibody stains, or for plots of the two antibody stains (FITC. vs AMCA) against each other.

Figure 7A:
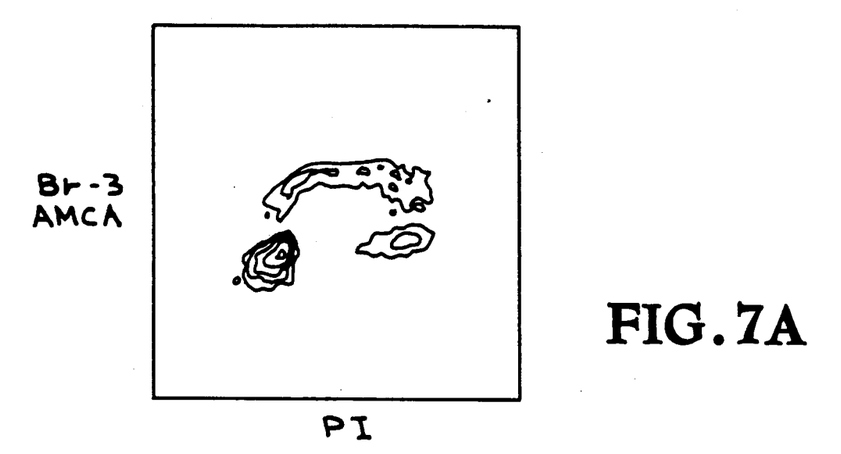
FIG. 7—Flow Cytometric Measurements of Separate BrdU incorporation in the presence of IdU incorporation. Cells grown for 30 minutes in IdU, 4 hours in normal medium, and then 30 minutes in BrdU, were stained with either AMCA-stained Br-3 antibody (Panel 7-A) or FITC-stained B-44 antibody (Panel 7-B) which was measured and plotted against total DNA content (PI). Cells stained with each antibody were plotted against each other (Panel 7-C).
Figure 7B:
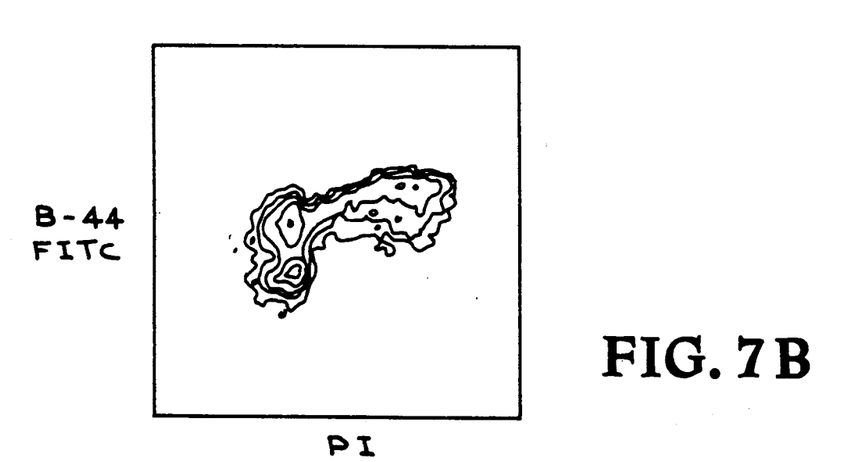
Figure 7C:
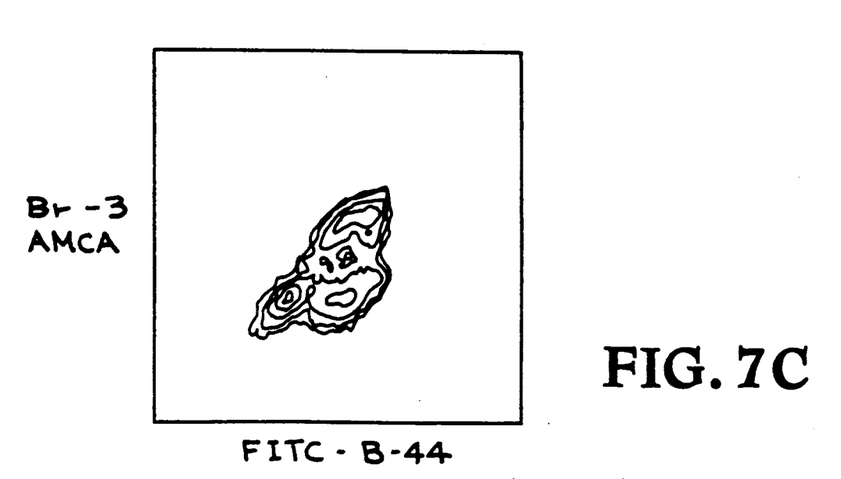

Three color fluorescent measurements of the labeling with two halogenated nucleoside analogs is illustrated in FIG. 7 A-C In panel A, the Br-3 antibody, which is visualized by the AMCA stain represents incorporated BrdU content (y-axis) plotted versus total DNA content stained with propidium iodide (x-axis). The staining pattern shows distinct peaks of cells representing the $G_1$, S and $G_2/M$ stages. Panel B shows the binding of the halogen specific monoclonal antibody B-44, which is identified by the FITC stain (y-axis), plotted against total DNA content (x-axis). B-44 antibody stains cells containing either incorporated IdU or BrdU. During the 4 hr growth period following the BrdU pulse, those cells with incorporated BrdU have progressed out of the S phase and through $G_2/M$ and division and into $G_1$ stage. The cells containing IdU are in S phase. The unlabeled cells are those which were not in a synthetic (S) phase during either pulse, and therefore did not incorporate either precursor. Panel C shows a histogram of cells which stained with AMCA-Br-3 (y-axis) plotted against those which stain with FITC B-44 (x-axis). Those cells which contain BrdU stain with both antibody immunochemical reagents. Those which contain only incorporated IdU stain only with B-44 immunochemical stain. Unstained cells contain neither analog.

9 Methods for Purification and Identification of Halogenated Nucleoside Analogs The antibodies herein developed may be covalently bound to a column and used to extract specific halogenated nucleoside analogs from samples which are eluted through the column. Subsequent elution and repeated extraction may be used to concentrate halogenated nucleoside analogs to remove them for further evaluation.

These examples confirmed that monoclonal antibodies produced by the hybridomas designated as Br-1, Br-3, and Br-5 are highly specific to halogenated nucleotide precursor analogs and binding values indicate recognition of a common epitope by these antibodies. The competition ELISA values indicate recognition of brominated nucleotide precursors at one hundred times the sensitivity as that of iodinated or fluorinated forms of these nucleotides. Such differential selectivity permits the use of these specific monoclonal antibodies for the separate detection of BrdU in the presence of other iodinated or chlorinated analogs. Less sensitive halogen-specific monoclonal antibodies can detect selective binding of bromine specific antibodies These antibodies can be used to identify, simply and conveniently, incorporation rates of nucleotide analogs into cells of one population while another population is monitored by incorporation of a different halogenated nucleotide analog.

The subject invention thus provides a method for determination of the proliferative fraction of multiple cell populations in a cell mixture. Monoclonal antibodies that are selective for a particular halogen can be used to identify and specifically distinguish the presence of halogenated nucleoside analog which contain different halogen molecules and are added at different times during the sampling period. The monoclonal antibodies of the preferred example bind preferentially to brominated deoxyuridine with a more than fifty fold greater specificity than to iododeoxyuridine. The monoclonal antibody with preference for bromine can be measured at substantially the same time that another general halogen-specific antibody is used. These monoclonal antibodies are useful for diagnostic applications where detection and quantitation of cell replication of more than one cell population is desired. They are contemplated to be useful for monitoring the sensitivity of multiple cell sub-populations to anti-tumor or anti-proliferative agents.

The above embodiments were chosen and described in order to explain best the principles and the practical applications of the subject invention thereby to enable those skilled in the art to utilize the invention in various other embodiments and various modifications as are suitable for the particular use contemplated. The foregoing description of some preferred embodiments of the invention, therefore, have been presented only for purposes of description and illustration of the subject invention. It is not intended to be exhaustive or to limit the invention to the precise forms disclosed, and many modifications and variations thereof would become obvious to those skilled in the art from the teachings and disclosure herein. It is intended that the scope of the invention is best defined by the appended claims.

We claim:

1. Monoclonal antibodies selected from the group consisting of Br-1, Br-3, and Br-5, which are deposited at the ATCC with Accession Nos. HB 10699, HB 10700 and HB 10698, respectively.

2. Hybridomas selected from the group consisting of Br-1, Br-3, and Br-5, which are deposited at the ATCC with Accession Nos. HB 10699, HB 10700 and HB 10698, respectively.